United States Patent [19]

Switalski et al.

[11] Patent Number: 5,386,295
[45] Date of Patent: Jan. 31, 1995

[54] POSTACQUIRED SPECTROPHOTOMETERS

[75] Inventors: Steven C. Switalski, Rochester; David S. Uerz, Ontario; Alan J. Lowne, Victor; James R. Sandifer; Hsue-Yang Liu, both of Rochester, all of N.Y.

[73] Assignee: Eastman Kodak Company, Rochester, N.Y.

[21] Appl. No.: 5,321

[22] Filed: Jan. 15, 1993

Related U.S. Application Data

[63] Continuation-in-part of Ser. No. 951,607, Sep. 28, 1992, Pat. No. 5,357,343, which is a continuation of Ser. No. 237,824, Jul. 26, 1991, abandoned, which is a continuation-in-part of Ser. No. 591,204, Oct. 1, 1990, abandoned.

[51] Int. Cl.$^6$ .................. G01J 3/02; G01N 21/64; G01N 21/65
[52] U.S. Cl. .................. 356/418; 356/301; 356/417; 356/419; 250/458.1
[58] Field of Search ............ 356/301, 416, 417, 418, 356/419, 317, 318; 250/458.1, 459.1, 461.1, 461.2

[56] References Cited

U.S. PATENT DOCUMENTS

| | | | |
|---|---|---|---|
| 3,780,299 | 12/1973 | Bock | 250/209 |
| 3,999,062 | 12/1976 | Demsky et al. | 250/227 |
| 4,061,428 | 12/1977 | Amano et al. | 356/175 |
| 4,097,743 | 6/1978 | Carlson | 250/339 |
| 4,305,663 | 12/1981 | Perkins et al. | 356/323 |
| 4,477,190 | 10/1984 | Liston et al. | 356/418 |
| 4,644,485 | 2/1987 | Ferber et al. | 364/569 |
| 4,648,714 | 3/1987 | Benner et al. | 356/301 |
| 4,945,250 | 7/1990 | Bowen et al. | 250/461.1 |

FOREIGN PATENT DOCUMENTS

291855A5  7/1991  Germany.

OTHER PUBLICATIONS

"In-Situ Measurement", IEEE Transactions, Jul. 1975, Konnerth et al.
Wetzel, D. L., "Near-Infrared Reflectance Analysis", Anal. Chem., 55(1983)1165A.
Stinson, S. C., "Advances Made in Applying IR Sensors to Process Control", Chem. and Eng. News, Jan. 1989, p. 30.
P. Dubois et al., "Determination of Five Components in a Pharmaceutical Formulation Using Near Infrared Reflectance Spectrophotometers", Analyst, vol. 112, p. 1675 (1987).
B. R. Buchanan et al., "Detection of Ethanol in Wines Using Optical-Fiber Measurements and Near-Infrared Analysis", Appl. Spect., vol. 42, p. 1106 (1988).
Instruction Manual, Microquad 8000, Nov. 25, 1984.
Konnerth, K. L., et al., "IOTA, A New Computer Controlled Thin Film Thickness Measurement Tool", 1972, vol. 15, pp. 271–380.
Hansen, G. L., "Introduction to Solid-State Television Systems, Color and Black & White", pp. 128—131.
Whalen, A. D., Detection of Signals in Noise, 1971, pp. 238–241.
Optical Coating Laboratory, Inc., Stock Filter Catalog, 1990–1991.

*Primary Examiner*—F. L. Evans
*Attorney, Agent, or Firm*—Clyde E. Bailey

[57] ABSTRACT

A postacquired spectrophotometer, for use with a sample and reference. The spectrophotometer has a filter unit, defining an axis of movement, and pluralities of designated sites and dark sites disposed in uniform relation to the axis. The designated and dark sites are disposed in alternation. Alternating designated sites have apertures and filters covering the apertures. Further, a main member, coaxial with the filter unit, has sample and reference beam paths, which are intersected by the sites. The main member has disposed, in operative relation to the actuators, an actuator sensor, which generates an integration actuator signal upon alignment with each integration actuator and a clamping actuator signal upon alignment with each clamping actuator. Moreover, a drive continuously moves the filter unit relative to the axis and beam paths. Further, a light distribution system directs light separately from the sample and reference to respective beam paths, and then to a detector, which produces a detector signal responsive to light received. Finally, means for processing the signals is provided, including a clamping circuit, integrators, and a demultiplexer.

26 Claims, 8 Drawing Sheets

POSTACQUIRED SPECTROPHOTOMETERS

CROSS REFERENCE TO RELATED APPLICATIONS

This application is a continuation-in-part of commonly assigned copending and allowed application Ser. No. 07/951,607 filed Sep. 28, 1992 by the present applicants, now U.S. Pat. No. 5,357,343; which is a continuation of Ser. No. 07/737,824 filed Jul. 26, 1991 and now abandoned; which was a continuation-in-part of Ser. No. 07/591,204 filed Oct. 1, 1990 and now abandoned.

FIELD OF THE INVENTION

The present invention relates to spectrophotometers and particularly relates to what are referred to herein as "postacquired spectrophotometers", spectrophotometers in which wavelength band selection is performed on light downstream from a sample, such as inelastic scattering and emission spectrophotometers. This can be contrasted to what can be referred to as "preacquired spectrophotometers" in which a wavelength band is first selected and then delivered to a sample. Inelastic scattering spectroscopy includes, but is not confined to, normal Raman spectroscopy, surface enhanced Raman spectroscopy, anti-Stokes Raman spectroscopy, and resonance Raman spectroscopy. Emission spectroscopy includes, but is not confined to, fluorescence, phosphorescence, chemiluminescence, bioluminescence, and other types of luminescence. In luminescent spectrophotometry, the light source is the sample. There are many applications for these types of spectroscopy, including chemical processing, bioprocessing, environmental, medical, and pharmaceutical applications.

BACKGROUND OF THE INVENTION

Spectrophotometers are known that use a single light source, a single detector and dual beam fiber optics that split the light into a reference beam and a sample beam. Such devices are shown, for example, in U.S. Pat. No. 4,061,428 and an article by Konnerth et al. entitled "In-Situ Measurement", IEEE Transactions (7/75). A common feature of such previous devices is the use of a filter unit wheel having apertured portions to allow both the reference beam and the sample beam to pass through a selected filter in the aperture. However, considering the device of the '428 patent, it is noteworthy that the triggering apertures 33 in filter unit wheel 22 are identical in number to the filter apertures 24. That is, there are disclosed 3N apertures 24 and 3N apertures 33. Further, the angular placement of apertures 24 is the same as such placement of the bifurcated fiber optics 17 and 14. As a result, the only way to prevent both the sample beam and the reference beam from arriving at the detector simultaneously (an unacceptable result), is to position an oscillating shutter 46 adjacent to filter unit 22. (Although there are N more apertures 38 also in filter unit 22, these are used to detect red versus green versus blue filters, and do not control whether a reference beam or a sample beam is in place). Such a use of a filter unit and a shutter has a decided disadvantage— there are at least two moving parts required, each of which is subject to wear and risk of breakdown.

In the Konnerth article noted above, there appears to be only one moving part in the spectrophotometer of FIG. 1, in which case a triggering mechanism would not be used to inform the computer as to the location of the filter unit. A highly accurate motor would, however, be required since the timing of filter unit rotation would have to be exact. For such an arrangement, the costs are high. A more preferred system is one in which the positioning can have wide tolerances because the actual rather than theoretical positioning is detected.

More recent attempts to provide spectrophotometers have not solved the noted problems. U.S. Pat. No. 4,648,714 teaches a dual beam spectrophotometer having a single moving part (filter unit 58 with four filter apertures 17(a)-17(d)). However, it does this at the expense of two detectors for reference and sample (19 and 37). The use of two different detectors is well known to be a source of drift error.

U.S. Pat. No. 4,097,743 teaches an optical system for a moisture analyzer in which two light beams are reflected at locations 180 degrees apart on a rotary wheel. The wheel has two filters and a window, all equally spaced 120 degrees apart. A series of mirrors are attached to the wheel at fixed positions, and provide signals to a sensor indicating wheel positions. Outputs are produced by the analyzer in the form of two time related pulse trains: a train of spaced pulses representing individual signals from each beam-filter combination and a train of periodic commutator pulses identifying wheel positions including a home position. The momentary pulses are used by a decoder circuit to separate the other pulse train, after amplification, into separate signals representing the beam-filter combinations. At the home position, a portion of the detection circuit is grounded, apparently providing an electronic "dark" signal. The decoded signals are combined, along with a reference voltage to provide a voltage representing sample moisture content which is displayed. This device has the shortcoming that detector related "noise", such as dark current, is not corrected for, in that the electronic "dark" signal is exclusive of the detector, which is grounded, regardless of whether or not residual photocurrent is flowing.

Some previous Raman spectrometers have used filters to attempt to provide a simple instrument. U.S. Pat. No. 4,586,819 teaches the use of a filter wheel with a laser and a monochromator. The filter wheel is used at an angle to the excitation laser beam and to the returning scattered Raman and laser signals from the sample. The device uses a laser oscillator to change the wavelength of the excitation beam. The function of the filters is to allow the reflected laser beam to pass on to a camera, and also to reflect the Raman scatter into a monochromator. The monochromator is used to select the Raman frequencies. Therefore, the filter wheel functions as a variable blocking filter, preventing the laser beam from entering the monochromator. It does not modulate the signal, switch from sample to reference, or select the Raman frequency for analysis. The instrument does not have a reference beam, and the light is not modulated. The monochromator, not the filter wheel, provides the frequency discrimination to obtain a Raman spectrum.

U.S. Pat. No. 4,648,714 teaches the use of a rotating filter wheel to select Raman frequencies to detect respiratory and anesthesia gases with one detector. The filter wheel serves only to provide a selection of Raman frequencies. A black filter is provided in the filter wheel for referencing the dark signal of the detector. Neither modulation nor switching between reference and sample beams is taught or suggested.

U.S. Pat. No. 4,784,486 is a Raman spectrometer in which multiple detectors and associated interference filters are used instead of a filter wheel to select Raman frequencies. This greatly complicates the device, and would not provide the advantages of stability and low cost sought for many applications.

Some luminescence spectrometers have used filters to provide a simple instrument. U.S. Pat. No. 3,999,062 uses a circular variable filter and a light path divided into a sample and a reference beam to provide an instrument to measure the amount of fluorescence. The instrument loops the light beams back through the filter wheel for a second pass, reducing the amount of space useful for wavelength selection. The wheel is designed such that a dark signal is not obtained. The main function of the device is to alternate between polychromatic and monochromatic excitation. This complexity requires a particular design for the light paths and a particular method to analyze the signal information, but does not lend itself to the purpose of providing a simpler instrument for general emission spectroscopy.

U.S. Pat. No. 4,477,190 teaches the use of two filter wheels that are synchronously rotated to provide light to multiple samples: the resultant light outputs from the samples are directed to multiple detectors. Although this provides a multichannel spectrophotometer, it does not provide a simple spectrometer, nor does it provide these capabilities from a single moving part.

U.S. Pat. Nos. 4,945,250 and 4,977,325 teaches the use of a filter wheel for a UV fluorescence spectrometer. It uses pairs of filters, thereby reducing the available space on the filter wheel for selection. Additionally, two detectors are used, incorporating an additional source of drift. The geometry of the housing is specifically designed for this filter wheel, and does not provide for a flexible modulating, switching, and wavelength selection component for luminescence spectroscopy.

U.S. patent application Ser. No. 737,824, filed Jul. 26, 1991, teaches a forward light source spectrophotometer which has a single moving part that requires only a single light source and a single detector and provides modulation, wavelength selection, and switching between sample and reference beams.

It is therefore desirable to provide a spectrophotometer which has dual sample and reference beams, filters for a variety of bands, corrects for unwanted signal, has a minimum of moving parts, and is relatively rugged, and stable.

SUMMARY OF THE INVENTION

In the broader aspects of the invention, there is provided a postacquired spectrophotometer, for use with a sample and reference. The spectrophotometer has a filter unit, defining an axis of movement, and pluralities of designated sites and dark sites disposed in uniform relation to the axis. The designated and dark sites are disposed in alternation. Alternating designated sites have apertures and filters covering the apertures. The filters each transmit only light of preselected wavelengths. The filter unit has a plurality of actuator pairs, each having an integration actuator and a clamping actuator. Each actuator is disposed in substantially uniform relation to the axis. The integration actuators are each associated with a respective designated site. A main member, coaxial with the filter unit, has sample and reference beam paths, which are intersected by the sites. The beam paths each have a cross-section at the filter unit interposable within each site. The main member has disposed, in operative relation to the actuators, an actuator sensor, which generates an integration actuator signal upon alignment with each integration actuator and a clamping actuator signal upon alignment with each clamping actuator. A drive continuously moves the filter unit relative to the axis and beam paths. A light distribution system directs light separately from the sample and reference to respective beam paths, and then to a detector, which produces a detector signal responsive to light received. A clamping circuit, in response to each clamping actuator signal, sets a restoration signal proportional to the detector signal. The clamping circuit, in response to each integration actuator signal, clamps the detector signal to the restoration signal. A demultiplexer distributes the clamped detector signal to a plurality of integrators. The demultiplexer has a single output, which advances from one of the integrators to another in repeating sequence in response to one of the members of each pair of actuator signals.

It is an advantageous effect of at least some of the embodiments of the invention that a spectrophotometer is provided which has dual sample and reference beams, filters for a variety of bands, corrects for unwanted signal.

BRIEF DESCRIPTION OF THE DRAWINGS

The above-mentioned and other features and objects of this invention and the manner of attaining them will become more apparent and the invention itself will be better understood by reference to the following description of an embodiment of the invention taken in conjunction with the accompanying drawings wherein:

FIG. 11 is a section view of a portion of the spectrophotometric device of the spectrophotometer of FIG.

10, taken generally through the axis of rotation of the filter unit.

DESCRIPTION OF PARTICULAR EMBODIMENTS

Figure 1:
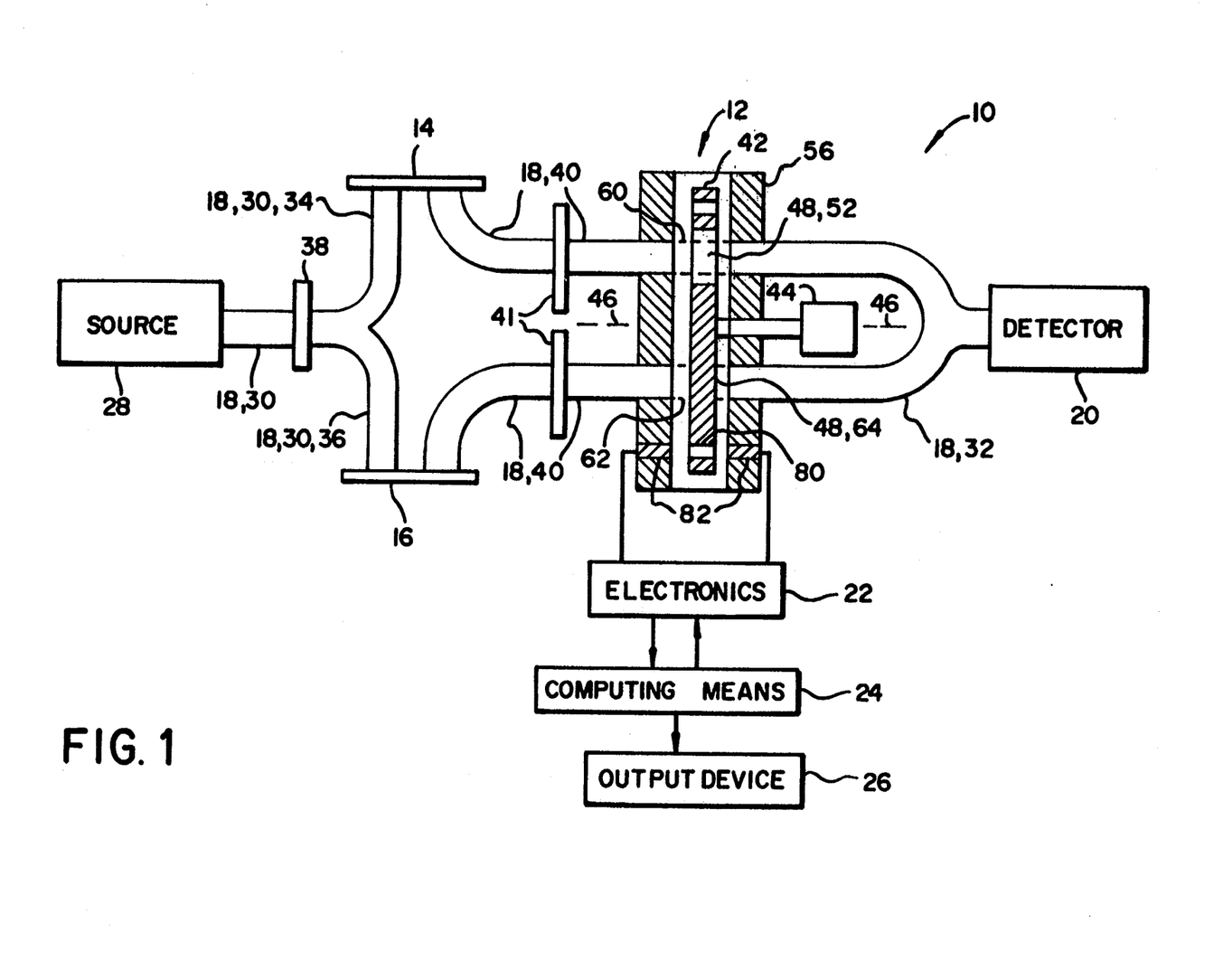
FIG. 1 is a schematic view of the overall construction of the spectrophotometer of the invention, the filter unit is in a position in which the sample beam path extends through a filter and the reference beam path is interrupted by a non-apertured designated site, some dimensions in schematics herein are exaggerated for clarity.

Referring to FIG. 1, the spectrophotometer 10 of the invention has a spectrophotometric device 12, described below in detail, which provides modulation, wavelength selection and switching of one or more pairs of sample and reference light beams. Spectrophotometer 10 directs light to a sample 14 and reference 16 and then through spectrophotometric device 12. Spectrophotometer 10 can be utilized, in an appropriate embodiment, as an inelastic scattering spectrophotometer, emission spectrophotometer or the like.

Spectrophotometer 10 has a light distribution system 18, a detector 20, associated electronics 22, computing means 24, an output device 26, and spectrophotometric device 12 and a light source 28.

Light source 28 is selected to provide a light having a suitable wavelength range for an intended use. Depending upon the embodiment of the invention, usable wavelength ranges extend from ultraviolet through infrared, 10–1,000,000 nm. Light sources suitable for particular embodiments include gas, excimer, dye, solid-state, and diode lasers; tungsten, tungsten-halogen, xenon, and deuterium lamps; and solid-state emitters, such as light emitting diodes, doped optical fibers, and doped substances.

Light distribution system 18 includes single optical fibers or fiber bundles which direct, split, and recombine the light beam, and may include auxiliary filters to provide non-varying filtration of the beam. As a matter of convenience, the terms "fiber" and "optical fiber" are used hereafter to designate both individual fibers and bundles of fibers. Fibers and light source are selected to meet the requirements of a particular embodiment of the invention while avoiding excessive attenuation and other degradation of the light transmitted. In a Raman spectrometer, for example, strong fluorescence within an entry fiber is deleterious (strong fluorescence in an exit fiber is much less deleterious since the amount of light traveling in exit fiber 32 is not typically enough to stimulate large amounts of fluorescence). Low fluorescence optical fibers such as Si/Ge fibers can be used to avoid this problem. Alternatively, an infrared light source at, for example, 780, 830, 980, or 1064 nm, can be used to achieve the same result.

Referring again to FIG. 1, entry fiber 30 receives the light beam from light source 28 and directs the beam to sample 14 and reference 16 along sample and reference arms 34,36, respectively; shown schematically in FIG. 1. The geometry of sample and reference arms 34,36 is not limited and can be modified by the use of fiber optic probes, such as bifurcated random bundles or bundles with particular geometries to enhance signal collection, such as excitation fibers in different orientations with collection fibers, gradient index and refractive lenses, and other optical elements such as mirrors, to change beam size, shape, and direction.

The light beam in entry fiber 30 may first be directed through a preconditioning filter 38 to remove unwanted wavelengths. For example, in a particular embodiment of spectrophotometer 10 configured for Raman spectroscopy, light source 28 is a laser or other monochromatic light source such as, for example, a 25 mW helium-neon laser that emits at 632.8 nm and preconditioning filter 38 is a laser line interference filter, designed to pass only the laser line and prevent other wavelengths including the plasma lines of the helium-neon laser from passing.

In embodiments of spectrophotometer 10 configured for use with a self-luminescent sample 14 and reference 16; light source 28, entry fiber 30, and preconditioning filter 38 are unneeded if it is unnecessary to change the luminescence signal.

Respective light beams can be directed through or reflected from sample 14 and reference 16. Light distribution system 18 may or may not include holders (not specifically illustrated) for sample and reference materials, depending upon the nature of the sample 14 and reference 16. The sample can be gas, liquid, or solid, including tissue, textiles, powders, pharmaceuticals, tablets, sheets, and chemical analytes in various forms. The reference can be a "standard", that is, a substance or configuration of substances that has an invariant composition with regard to the type of spectroscopy performed and can provide for a signal at appropriate wavelengths. Such a standard could be a liquid, solid, or gas that has been encapsulated to prevent degradation by the environment (for example, a glass vial of an inorganic salt, such as potassium nitrate, that has been purified and sealed under vacuum). Such a standard could also include the optical components of the reference arm 36 itself, for example, the reference arm 36 could include an optical fiber or a glass lens in which appropriate Raman lines could be excited. In one type of Raman spectrophotometer 10, reference 16 is a reflective substrate, such as a mirror, or a diffusely reflective substrate, such as an alumina ceramic plate. A separate attenuator, such as a neutral density filter, can be included to reduce the level of the reference beam or the reference 16 itself can provide attenuation to balance the level of the reference beam.

Intermediate fibers 40 receive light from reference 16 and sample 14 and direct beams to spectrophotometric device 12. In particular embodiments of spectrophotometer 10, beams may first be directed through conditioning filters 41 to remove extraneous portions of the beams. In particular embodiments of spectrophotometer 10, conditioning filters 41 are used with and complementary to preconditioning filter 38, that is, conditioning filters 41 remove all the intensity at those wavelengths that were allowed to pass to the reference 16 and sample 14 by preconditioning filter 38. For example, in a particular embodiment of a Raman spectrophotometer 10, conditioning filters 41 are notch filters which remove the source excitation wavelength. In another embodiment of spectrophotometer 10 in which phosphorescence is monitored, conditioning filters 41 reduce fluorescent light to permit easier measurement of wavelengths with phosphorescence intensity.

Exit fiber 32 receives beams from spectrophotometric device 12 and recombines reference and sample beams before delivering beams to detector 20.

Optical fibers 30,32,40 can be replaced by air paths and mirrors and can be otherwise varied to meet the requirements of a particular spectrophotometer 10. Preconditioning filter 38 and conditioning filters 41 can similarly be modified or deleted and additional filtration elements can also be used.

Referring now to FIGS. 1, 2, 3, and 4, spectrophotometric device 12 has a main member 56 and a filter unit 42; a motor 44, which rotates filter unit 42 about an axis of movement 46. Rotation is shown in the figures as being counterclockwise, however, the direction or directions of movement are not important to the operation of spectrophotometer 10.

Figure 3:
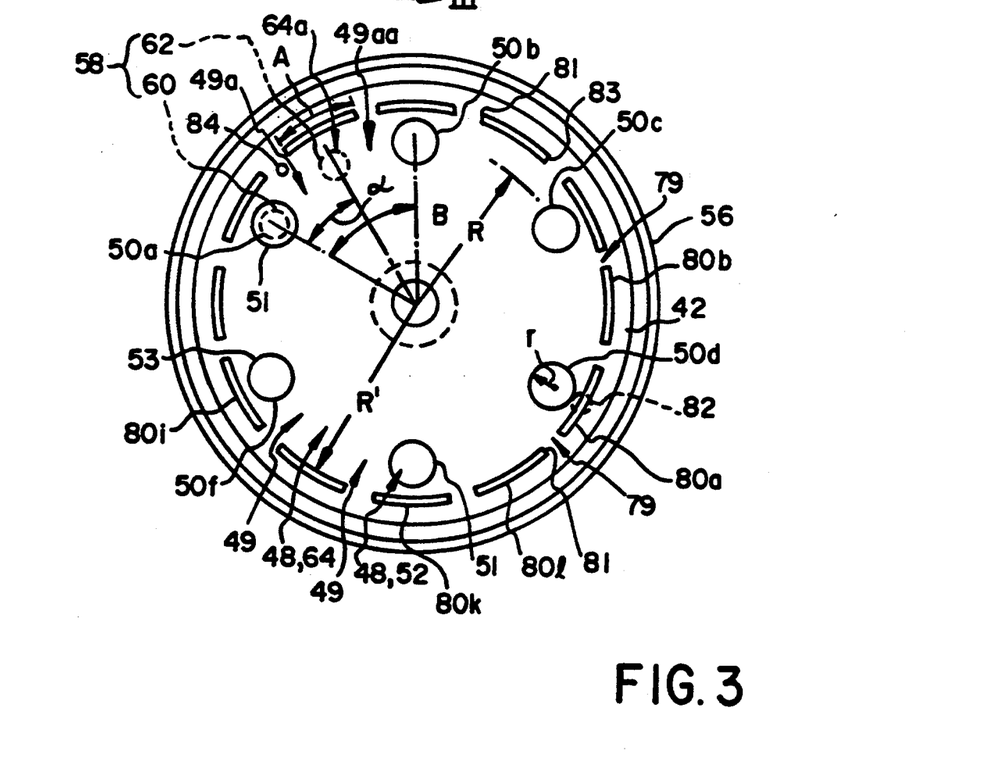
FIG. 3 is a section view taken generally along the line III—III of FIG. 2; the filter unit is in a position in which the sample beam path extends through an aperture bearing a bandpass filter and the reference beam path intersects a non-apertured designated site.
Figure 4:
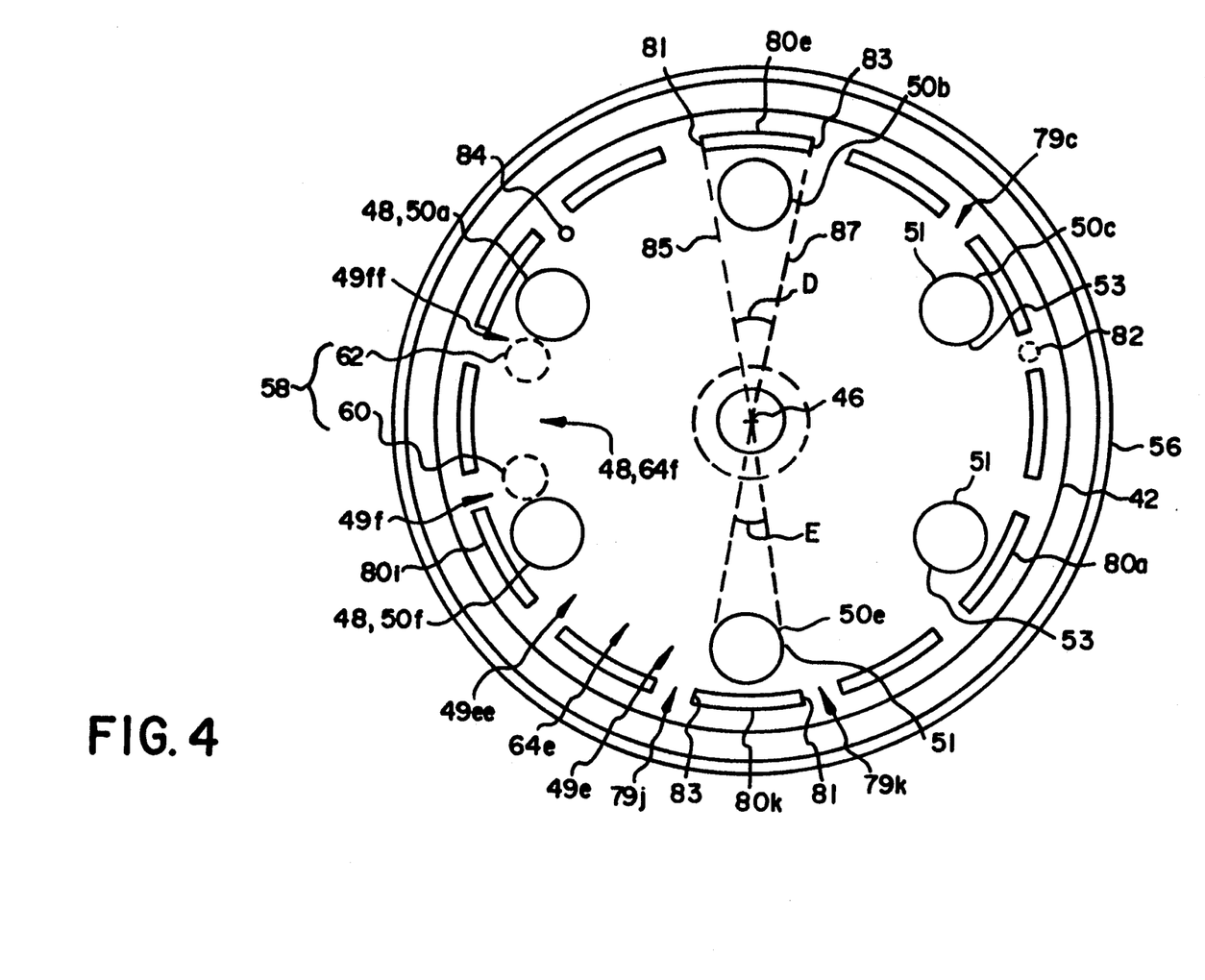
FIG. 4 is a section view taken generally along the line III—III of FIG. 2; the filter unit is in a position in which neither the sample beam nor the reference beam path intersects a designated site.

Filter unit 42 has a plurality of designated sites 48 disposed at a uniform separation from axis 46. Designated sites 48 are disposed in a ring encircling axis 46. Between neighboring designated sites 48 are dark sites 49. Alternate designated sites 48 have apertures 52. Apertured designated sites 50 each have a leading edge 51 and a trailing edge 53.

Bandpass filters 54 occupy each apertured designated site 50. Filters 54 are selected based upon the requirements of a particular use. Each bandpass filter 54, can be selected to transmit a different band of wavelengths. For example, the bandpass filter 54 in apertured designated site 50a can pass the wavelengths 1296±5 nm, the one in apertured designated site 50b the wavelengths 1360±5 nm, and so forth for apertured designated sites 50c, 50d, 50e, and 50f. For example, in particular embodiment of a Raman spectrophotometer 10, bandpass filters 54 are selected to pass different Raman frequency shifts from the laser line.

Filter unit 42 has a plurality of pairs of integration actuators 80 and clamping actuators 79 which are disposed in a band at a substantially constant radial separation from axis 46. Each integration actuator 80 has an initiation end 81 and each clamping actuator 79 has an initiation end 83. Each actuator 80,79 can have the minimal length in the direction of rotation of filter unit 42 necessary to generate a momentary signal, as below discussed. It is desirable, however, that each actuator 80,79 have a finite length which can provide a signal of some duration. In the embodiments of the invention shown in the Figures, each actuator 80,79 extends along filter unit in a direction of movement of filter unit 42 relative to beam paths 60,62. In the embodiment of the invention shown in FIGS. 3 and 4 each integration actuator 80 is an arcuate slot or mirror and defines an arc of a circle centered on axis of movement 46. Actuators 79,80 are located at a radius $R^1$ from axis 46, and the band of target and dark sites 48,49 are located at a radius R from axis 46.

Figure 2:
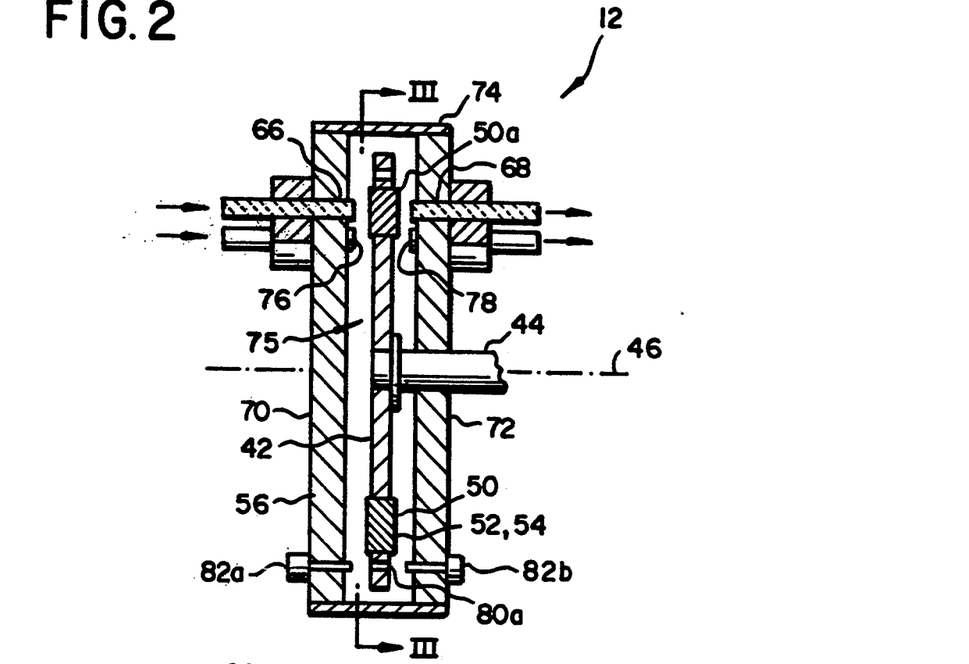
FIG. 2 is a section view of a portion of the spectrophotometric device of the spectrophotometer of FIG. 1, taken generally through the axis of rotation of the filter unit.

Main member 56 is coaxial with filter unit 42. Main member 56 has opposed first and second members 70,72 joined by a housing 74, which together defines a chamber 75 enclosing filter unit 42. In main member 56, intermediate fibers 40 terminate at ends 66,76 respectively, which are held by first member 70. Second member 72 holds ends 68,78 which are the initiation points of exit fiber 32. Ends 66,68,76,78 desirably include end elements (not shown) which function as wave guides, such as quartz rods or GRIN lenses. Ends 66,76 of intermediate fibers 40 are aligned with respective ends 68,78 of exit fiber 32. Ends 66,76 and 68,78 are also aligned with the ring of sites 48,49 on filter unit 42. Pairs of ends 66,76 and 68,78 define a beam path pair 58: sample and reference beam paths 60,62, respectively. Beam paths 60,62 are defined as the volumes within chamber 75 traversed by sample and reference light beams, when those beams are transmitted between ends 66,76 and 68,78, and are not interrupted by filter unit 42. Main member has a sensor 82 (described below in detail), which faces the band of actuators 80,79 of filter unit 42. In a preferred embodiment of the invention, beam paths 60,62 and sites 48,49 have relative sizes which permit dark sites 49 and designated sites 48 to each accommodate beam paths 60 and 62, without overlap onto a neighboring site 48 or 49.

Sample and reference beam paths 60,62 remain fixed relative to axis 46 during rotation of filter unit 42. The relative spatial relation between sample beam path 60 and reference beam path 62 is the same spatial relation as between an apertured designated site 50 and a non-apertured designated site 64. In the embodiment of spectrophotometer 10 of FIG. 3, these relationships are angular dimensions, which can be defined for the beam paths 60,62 and the pair of designated sites 50,64, respectively, as: an angular dimension centered on axis 46 and the centers of beam paths 60,62; and angular dimensions centered on axis 46 and centers of a pair of designated sites 50,64. Referring to FIG. 3, designated sites 48 are disposed with their centers on a radius R, and are angularly disposed evenly about the 360°, at an angle $\alpha$ between neighboring designated sites 48. The angle between neighboring apertured designated sites 50 is $\beta$, which is two times $\alpha$. Members of a beam path pair 60,62 have a relative angular dimension which is equal to an odd number multiple of $\alpha$, the angle of designated site offset.

Since it is desirable to minimize the time lag between sample and reference readings it is desirable that the angular separation of beam paths 60,62 be less than 180 degrees and more desirable that the relation be the same angular relation as between neighboring designated sites 48. This is the case in the embodiment of the invention shown in FIG. 3, in which the relative angular separation of members of beam pair 60,62 is 30° and the values of $\alpha$ and $\beta$ are 30° and 60°, respectively.

Specific angles of $\alpha$ and $\beta$ are determined by the size of sites 48,49. For a given radius R of the center of each apertured designated site 50 having a given radius r and for a given size of radius of the beam paths 60,62, there is a maximum number of apertured designated sites 50 which, when evenly distributed angularly at that radius R of centers, one cannot exceed without eliminating dark sites 49 and destroying the "dark time", the time when neither the reference beam nor the sample beam transmits through the filter unit 42. Alternatively, for given angles $\alpha$ and $\beta$, the sizes of beam paths 60,62 and apertures 54 are limited. The beam sizes and aperture widths provide relative angles $\gamma$ and $\gamma'$, such that $\gamma' \geq \gamma$, shown in FIG. 11 for a multiple sample embodiment of spectrophotometer 10, discussed below in detail. As is apparent from FIG. 11, $\gamma'$ is that angle defined by $(A+dt)/R^1$, where dt is the smaller of the beams emanating from intermediate fibers 40 and detected by exit fiber 32, and $\gamma$ is that angle defined by $(2r+d)/R$, where each apertured designated site 50 has a radius of dimension "r", and d equals whichever beam diameter of fibers 40,32 is the largest.

The rotation of filter unit 42 about axis 46 causes beams to be directed continuously toward beam paths 60,62, but what emerges from filter unit 42 is a multiplexed beam which in which light and dark periods alternate and light periods alternate between sample and reference beams. FIG. 3 illustrates filter unit 42 in a position in which a beam along sample beam path 60, passes through the bandpass filter 54 in apertured designated site 50a, and a beam along reference beam path 62 is interrupted by non-apertured designated site 64a. FIG. 4 shows filter unit 42 in a position in which a beam along sample beam path 60, is interrupted by dark site 49f and a beam along reference beam path 62 is interrupted by dark site 49ff. As filter unit 42 continues to rotate in a counter-clockwise direction, beam paths 60,62 face apertured designated site 50f and non-apertured designated site 64f, respectively. The beam paths 60,62 next face dark sites 49ee and 49f, respectively. This sequence of sample beam, dark, reference beam, dark; then repeats as rotation of filter unit 42 continues and filter unit 42 returns to a starting or "home" position for the next cycle.

Spectrophotometric device 12 is described herein generally in relation to a pair of sample and reference beam paths 60,62 and a single detector 20. The invention is not limited to a single sample beam path 60 in association with a single reference beam path 62. For example, a spectrophotometer 10 can have a single detector and two sample beam paths 60 and a single reference beam path 62 or two beam path pairs 60,62. In such embodiments of spectrophotometer 10, light distribution system 18 is appropriately modified. In order to avoid the use of a separate moving part, that is, a shutter, to alter which beam is being detected by an individual detector 20, a particular relationship is needed between the number of apertured designated sites 50, the number of beam paths, the number of integration actuators 80, and the number of sensors 82. More specifically, if N=number of apertured designated sites 50 (containing bandpass filters 54), n=the number of beam paths, q=number of integration actuators, and Z=number of sensors, the following equation holds:

(2) $n \times N = q \times Z$

In a particular embodiment of the invention, for example, n=2, N=6, q×Z=12, q=1 and Z=12. A multiple sample embodiment of spectrophotometer 10 is described below, in which multiple detectors are used. In that embodiment, the above equation holds for elements associated with each detector 20.

Referring now particularly to FIGS. 2-4, integration and clamping actuators 80,79 are positioned so as to be in operative relation to sensor 82 when a pair of designated sites 48 are aligned with a beam path pair 60,62. Sensor 82 is disposed on main member 56 at radius $R^1$. Sensor 82 and actuators 80,79 together comprise a sensing means. Sensor 82 can comprise a suitable number of energy emitters 82a and detectors or integration photodiodes 82b. Integration actuators 80 can comprise energy relays on filter unit 42 that allow the energy of emitter 82a to reach detector 82b and clamping actuators can comprise energy blocking elements that prevent the energy of emitter 82a from reaching detector 82b. Integration actuators 80, for example, can be slots which transmit light or reflectors and clamping actuators 79 can be nontransmitting or non-reflective portions of filter unit 42, respectively. Sensor 82 signals alignment with integration actuators 80 by transmitting an integration actuator signal and with clamping actuators 79 by transmitting a clamping actuator signal. In the embodiments of the invention of the Figures, integration actuator signal is an "on" or transmitting signal and clamping actuator signal is an "off" or nontransmitting signal.

Integration actuators 80 are each associated with a respective designated site 48 and are each disposed at a uniform angular offset from that designated site 48. In the embodiment of spectrophotometer 10 shown in FIGS. 3 and 4, the angular offset from sample beam path 60 is 180 degrees. When an integration actuator 80 is in an active position, that is, aligned with sensor 82, one of a pair of designated sites 48 is disposed in the reference beam path 62 and the other member of the pair of designated sites 48 is disposed in the sample beam path 60.

Referring now to FIG. 4, initiation ends 81,83 of actuators 80,79 define actuator axes 85,87, respectively, which are perpendicular to axis of movement 46 (indicated by a cross in FIG. 4). Axes 85,87 are only shown in FIG. 4 for actuators 80k,79k. Integration actuator 80k is associated with apertured designated site 50b. Actuator axes 85,87 have a separation in a direction of movement of filter unit 42 which defines the angular dimension of integration actuator 80, referred to herein as the "actuator dimension", indicated by a "D" in FIG. 4. Leading and trailing edges 51,53 of each apertured designated site 50 define leading and trailing axes 89,91, which are each perpendicular to axis of motion 46. Leading and trailing axes 51,53 have a separation in a direction of movement of filter unit 42, which defines the angular dimension of the designated site 48, referred to herein as the "designated site dimension", indicated by an "E" in FIG. 4, for axes 51,53 of designated site 50b. Actuator dimension D is at least as large as designated site dimension E and is preferably substantially the same size. The result, as discussed in greater detail below, is that integration of signals relating to each designated site 48 occurs during the entire travel of that designated site through a beam path 60 or 62, but only during that travel.

Actuators 80,79 rotate about axis 46 and pass successively into and out of alignment with sensor 82. In a particular embodiment of the invention, the sensing means comprises a light emitter 82a, a photodetector 82b, twelve integration actuators 80a-80l, and twelve clamping actuators 79a-79l. In this embodiment, integration actuators 80a-80l are slots and have an arc A of open area. The signal from emitter 82a is sent through integration actuator 80a when a pair of target and dark sites 48,49 are aligned with ends 66,76,68,78 of fibers 32,40. Light is transmitted from an intermediate fiber 40 to exit fiber 32 only when an interposed designated site 48 is apertured and has a filter 54.

A hole or discontinuity 84 is provided anywhere in filter unit 42, for example, at a radius that causes it to be positioned in between the ring of actuators 80,79 and the ring of sites 48. Hole 84 cooperates with a separate emitter and receiver, (shown as photodiode 101 in FIG. 5) which is used to signal that filter unit 42 is in the "home" position. The function of hole 84 can be assumed by actuators 80,79 for example, by the use of integration actuators 80 with reflecting surfaces, one of which is darker or lighter than the others and appropriately clamping the output of the detector 82b.

Figures 5, 6:
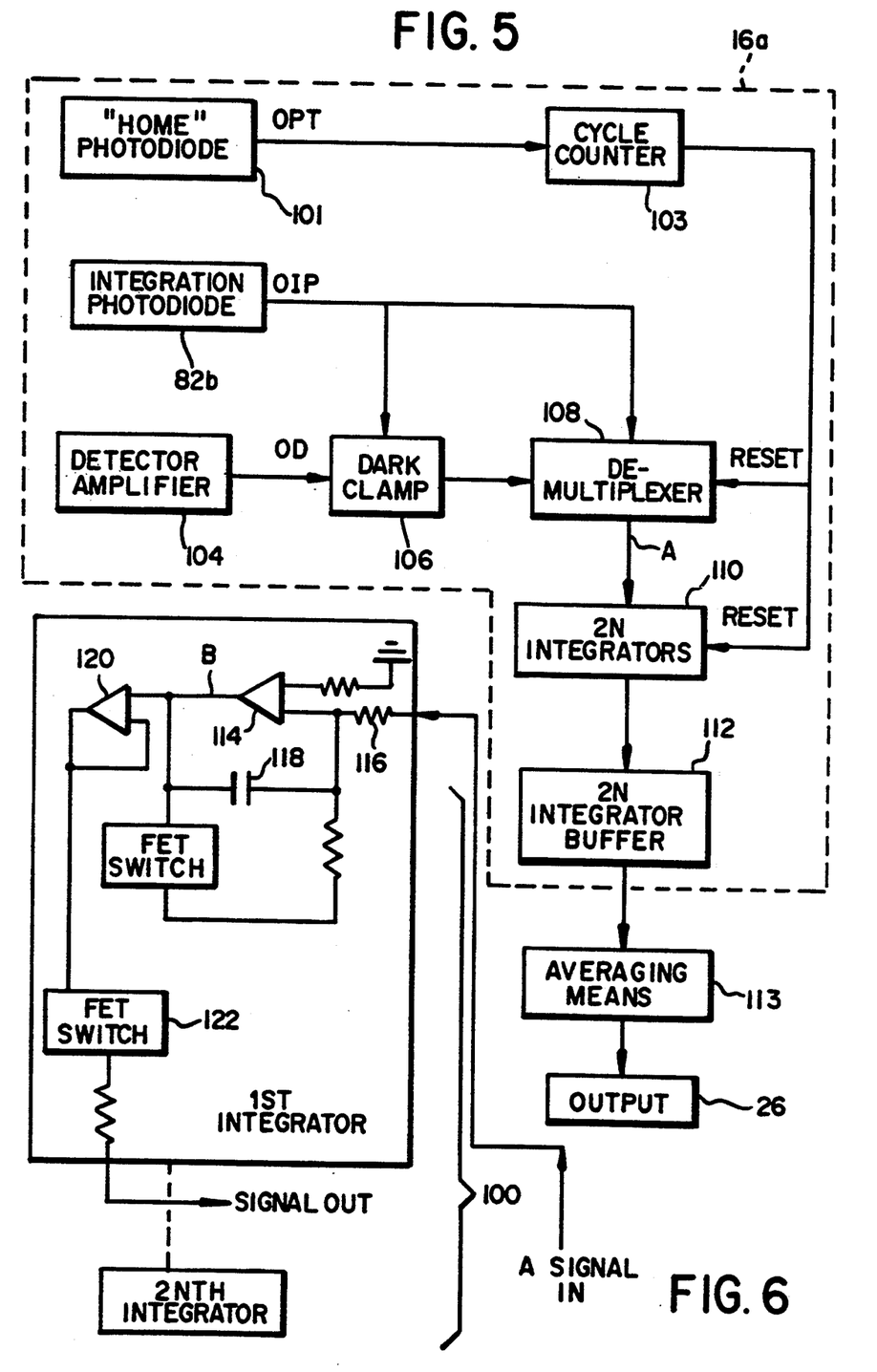
FIG. 5 is a schematic diagram of the associated electronics used with the remainder of the spectrophotometer illustrated in FIG. 1.
FIG. 6 is an expanded circuit diagram of the integrator portion of the diagram of FIG. 5.

Electronics 22 is shown in a schematic in FIG. 5. Unless otherwise specified, all electrical components and circuits herein are conventional and are designed for optimum signal-to-noise ratios. Component 16a incorporates elements 82, 101, 103, 104, 106, 108, 110, and 112. Photodiode 101 provides a home signal when filter unit 42 is in a "home" position. Sensor 82 provides integration actuator signals and clamping actuator signals. A cycle counter 103 counts the total number of cycles between resets.

An amplifier 104 receives a signal from detector 20. The beams from spectrophotometric device 12 combine, as shown in FIG. 1, to provide a multiplexed signal of sample beam, dark, reference beam, dark, cycles. The signal provided by detector 20 is multiplexed in the same way.

A clamping circuit 106, identified as "dark clamp" in FIG. 5, receives a signal from both sensor 82 and amplifier 104, and feeds to a demultiplexer 108. Clamping circuit 106 is a conventional DC restorer clamping circuit. In response to a clamping actuator signal clamping circuit 106 sets a restoration voltage or signal at the same level as the signal provided by amplifier 104. This "dark level" represents the signal originating in detector 20 when both beam paths 60,62 are blocked by a pair of dark sites 49. In the absence of a clamping actuator signal, that is, when a beam is transmitted through an apertured designated site 50 along one of beam paths 60,62, clamping circuit 106 clamps the detector signal to the restoration signal. In other words, each light pulse in the detector signal is dark clamped to a restoration signal set by the preceding dark pulse. The dark clamping compensates for dark current and for extraneous signals. The very short delay between setting the restoration level and dark clamping the succeeding light pulse, reduces the effect of variability in detector 20 and related circuitry.

Demultiplexer 108 distributes the clamped detector signal to integrators 110. Demultiplexer has a single output, which advances from integrator 110 to integrator 110 in repeating sequence. Each advance of demultiplexer output is in response to either integration actuator signals or clamping actuator signals. It is preferred that demultiplexer output advance in response to clamping actuator signals. Since the detector signal is not being accumulated by an integrator 110 during dark clamping, possible signal loss due to an overlap between demultiplexer output advance and integration is avoided.

Each integrator 110 accumulates its distributed portion of the clamped detector signal output by demultiplexer. Demultiplexer 108 utilizes a "home" signal provided by home photodiode 101 to initialize each cycle and ensure that each integrator 110 receives only that portion of detector signal due to a single combination of beam path 60 or 62 and filter 54. Each integrator 110 remains allocated to the same apertured designated site 50 in each cycle unless the electronics are reset. The number of integrators 110 is equal to the number of combinations of beams, indicated herein as "n" and the number of apertured designated sites 50, indicated herein as "N"; that is nN. If there is one sample beam path 60 and one reference beam path 62, that is n=2, then there are N integrators 110 for the sample beam and another N integrators 110 for the reference beam.

Each integrator 110 preferably feeds to an integrator buffer 112. From there the signal is sent to averaging means 113, so that an average can be taken for each combination of beam and apertured designated site 50. Averaging means 113 is preferably a portion of computing means 24, for example, a conventional computer. The final results are directed to output device 26. Alternatively, the averaging step and use of means 113 can be omitted, so that an instantaneous reading of each integrator 110 assigned to specific bandpass wavelengths, is sent to output 26 after a single revolution or reciprocation of filter unit 42.

Figure 7:
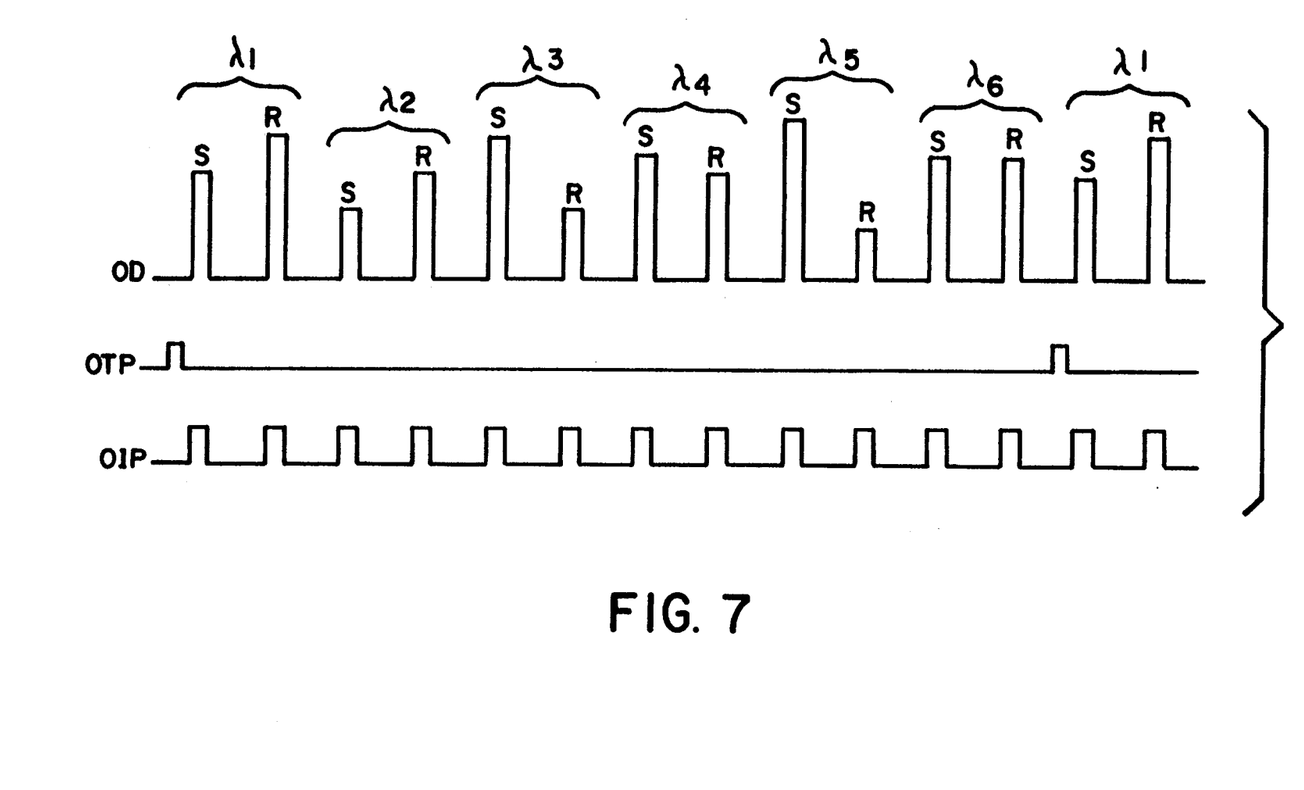
FIG. 7 is a schematic illustration of the outputs of the detector (OD), the home sensor (OTP) and the trigger or integration photodiodes (OIP)

The signal generated by the electronics components set forth in FIGS. 5 and 6 is shown in FIG. 7. The width of the peaks of the OIP signal coming from detector 20 is preferably only slightly larger than the width of the peaks of the OD signal coming from detector 20, although the width of the OIP peaks could be greater since any dark reading before or after an aperture transmits, should contribute no substantial signal. OIP signal widths that are less than the widths of the OD signal are not desired because performance is degraded. "S" represents a sample reading; whereas "R" is a reference reading. Each of the $\lambda_i$ values is, of course, a narrow range of values, rather than one single wavelength.

FIG. 6 further illustrates a suitable circuit for each of the 2 N integrators 110. They comprise an amplifier 114 that receives the signal A from demultiplexer 108 through a resistor 116. Output B is used to charge capacitor 118 to a value that represents the actual light detected. The voltage created by that charge is then read through amplifier 120 and FET switch 122 and sent as the signal out that represents the reading for one complete set of cycles of filter unit 42 at that bandpass wavelength.

Figure 10:
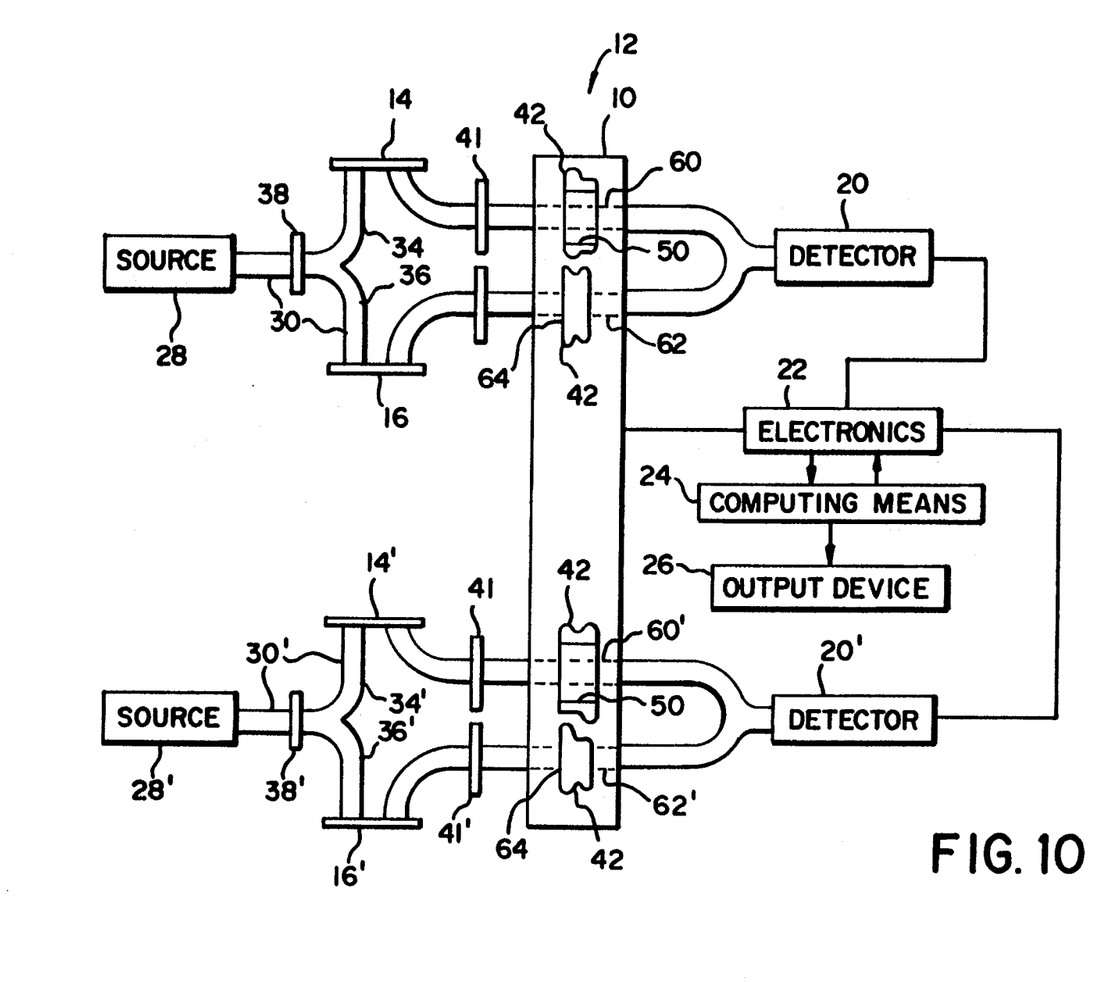
FIG. 10 is a schematic view of a multiple sample spectrophotometer of the invention; the filter unit is shown cut away and rearranged for clarity.
Figure 11:
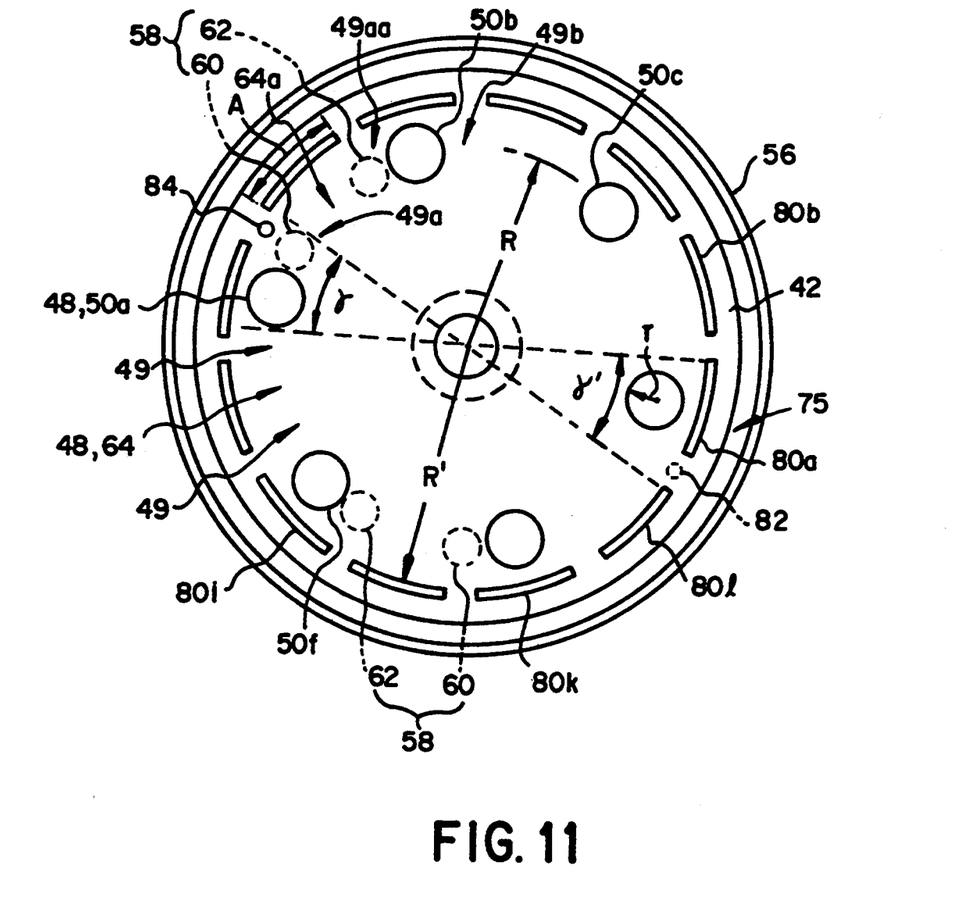

Referring now to FIGS. 10-11, in a particular embodiment of the invention, spectrophotometer 10 is a multiple sample spectrophotometer having a single spectrophotometric device 12, but light distribution system 18, detector 20, and any light source 28, are duplicated one or more times (shown in FIG. 10 as elements 18,20, and 28, respectively). Electronics 22, computing means 24, and output device 26 may be duplicated or the multiple signals can be accommodated by other means, for example, by multiplexing. In this embodiment, each duplicate 18 of light distribution system 18, is associated with an additional beam path pair 60,62 in spectrophotometric device 12. Each beam path pair 60,62 and 60',62' and associated components provides an individual signal, as if a series of independent spectrophotometers 12 were provided rather than just one. FIG. 10 shows duplicate samples 14,14', references 16,16', and reference beam paths 62,62', however, other arrangements could be provided. For example, a reference 16 or reference beam path 62' could be shared or readings could be taken at different or the same locations on a single sample 14. Multiple sample spectrophotometer 10 is shown, in FIG. 10, as having spectrophotometric device 12 located between samples 14,14' and detectors 20,20' however, the multiple sample spectrophotometer 10 of the invention could also have spectrophotometric device 12 positioned between sources 28,28' and samples 14,14". This would be illustrated by FIG. 10, if sources 28,28" and detectors 20,20' (and associated electronics 22, computing means 24, and output device 26) were exchanged and filters 38,38',41,41' were rearranged as appropriate for a particular use.

Referring now to FIG. 2, gain correction can be provided, in some embodiments of spectrophotometer 10 by including an additional pass-through filter 54 which provides an intensity value at the wavelength of the exciting light. The signal passed by this filter 54 can be ratioed with the other reference and sample signals to provide the gain correction. This signal also provides a monitor of fluctuations of intensity of the light source 28. If light source 28 is a laser, this reduces the amount of time that must be used to allow the laser to warm up. Additionally, if the laser is a solid-state, diode, or other temperature-sensitive device, thermostating of the light source 28 is not as important because of this ability to correct source drift. Gain correction can also be provided by the use of a standard for reference 16, as discussed above, rather than a reflective substrate or the like. If a standard is used, then a filter 54 at the wavelength of the source excitation is not necessary. The use of a standard in reference arm can also provide a correction for a drift in the exciting wavelength of the light source 28. Since Raman scattering wavelengths are measured relative to the source, if there is a drift in the wavelength of the source, there is a drift of the wavelengths at which the Raman scattering occurs. Because the wavelengths of pass-through filters 54 are fixed, the drift in the Raman wavelengths would be observed as a change in the intensity of the light transmitted. Use of a standard for reference 16 permits correlation of changes in excitation frequency to correct for wavelength drift.

It will be readily appreciated that, by a comparison at each of N different groups of wavelengths, of the sample signal against the reference signal, a determination can be made, using conventional mathematics, of the presence (and amount) of certain chemicals that are present at the sample 14. Most importantly, this is accomplished with a single light source 28 and detector 20 for each beam path pair 60,62, to minimize drift; and optics to include a reference reading; and only one moving part (filter unit 42) to minimize breakdowns. By having the reference 16 be read very close in time to the sample read, e.g. within a few milliseconds for filter unit 42 being rotated at 1500 RPM, the potential for drift is further minimized.

It is not necessary that the filter unit 42 of this invention be rotated or that the path of the pass-through apertured designated sites 50 be circular. FIGS. 8A–8E and 9 illustrate components of a spectrophotometer 10 that is reciprocated. Referring to FIGS. 8A–8E, spectrophotometer 10 includes a generally rectangular filter unit 42 having an axis of movement 46 and designated sites 48 arrayed along axis 46 at a uniform offset from each other, with dark sites 49 therebetween. Alternate designated sites 48 bear apertures. Each apertured designated site 50a–50c is fitted with an appropriate bandpass filter 54. Filter unit 42 is reciprocated relative to a beam path pair 58, here illustrated as inked spots 60 and 62 on filter unit 42. The "+" designates the location of sensor 82 and the lines above the filters 54 represent integration actuators 80.

Figure 8A:
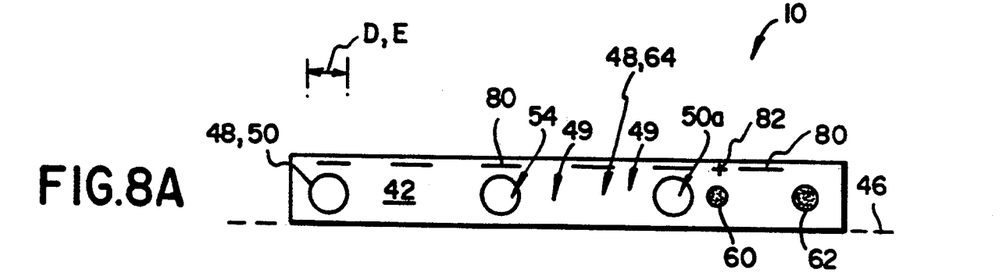
FIGS. 8A–8E are schematic illustrations of the invention using a linear filter unit that is reciprocated.
Figure 8B:
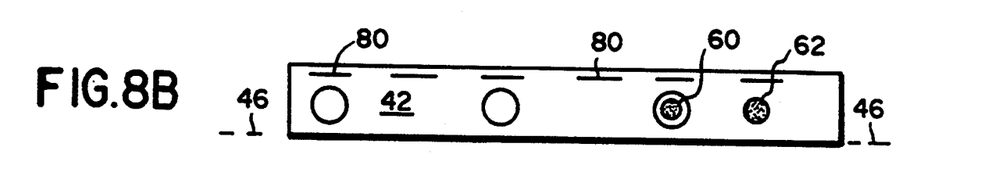
Figure 8C:
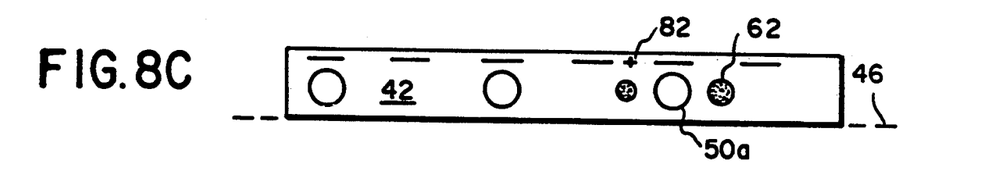
Figure 8D:
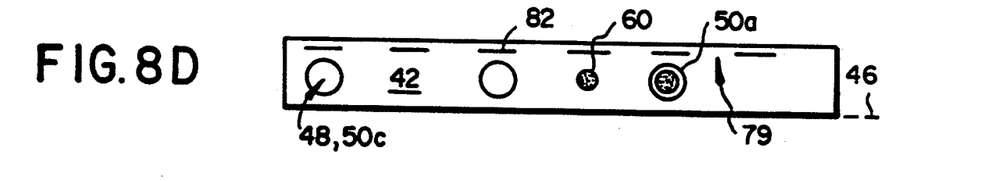
Figure 8E:
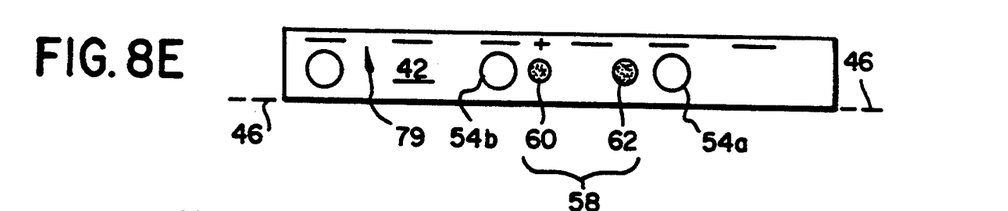

FIGS. 8A–8E show: (8A) both beam paths 60,62 interrupted by dark sites 49 (dark time), (8B) sample beam path 60 transmitted through filter 54 and reference beam path 62 interrupted by non-apertured designated site 64, (8C) both beam paths 60,62 interrupted by dark sites 49, (8D) sample beam path 60 interrupted by non-apertured designated site 64 and reference beam path transmitted through filter 54, and (8E) both beam paths 60,62 interrupted by dark sites 49. Sensor 82 is aligned with an integration actuator 80 in FIGS. 8B and 8D. FIG. 8E is analogous to FIG. 8A in that both represent dark times.

The necessary conditions for the reciprocating spectrophotometer are the same requirements that apply to the circular version, with the exception that angular dimensions relative to an axis of rotation 46 are replaced by linear dimensions relative to longitudinal axis 46. Dark sites 49 must be large enough to accommodate beam paths 60,62. That is, as shown in FIGS. 8A–8E, beam paths 60,62 must fit completely between neighboring designated sites 48 during dark times. Other considerations discussed above in relation to the rotary spectrophotometer also apply to the reciprocated device, for example, a reference beam path can be shared with more than one sample beam path.

Figure 9:
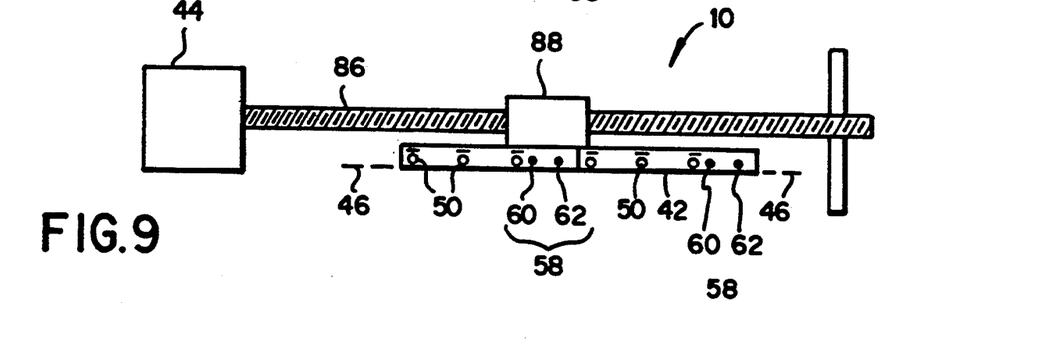
FIG. 9 is a fragmentary schematic view of a drive for a linear filter unit.

FIG. 9 shows a reciprocated multiple sample spectrophotometer 10 in diagrammatical form. An elongate filter unit 42 includes two repeats of the filter unit structure illustrated in FIGS. 8A–8E. The location of the main member is indicated by inked spots representing two beam path pairs 58. Filter unit 42 is caused to reciprocate, along axis 46, for example, by a conventional stepper motor 44, FIG. 9, which rotates a lead screw 86, that in turn causes a carrier plate 88 to reciprocate, filter unit 42 being attached to plate 88. This causes the filter unit 42 to reciprocate relative to beam path pairs 58. Stepper motor 44 could be replaced with a vibratory motor.

In an example of a particular embodiment of a rotating spectrophotometer 10 for use in Raman spectroscopy, light source 28 was a helium-neon laser, preconditioning filter 38 was a helium-neon interference filter, conditioning filters 41 were complementary, light distribution system 18 used single or bundle optical fibers, filter unit 42 utilized an aluminum plate, about 15 cm in diameter and 0.33 cm thick, filters 54 were 1 nm FWHM bandpass, CWL tolerance 0.5 nm, 30% transmission, blocking complete within 0.01%T, motor 44 was a brushless DC servo, and detector 20 was a photomultiplier tube.

In an example of a particular embodiment of a rotating spectrophotometer 10 for use in luminescence spectroscopy, light source 28 was a tungsten-halogen lamp, preconditioning filter 38 was a shortpass filter, conditioning filters 41 were longpass filters, light distribution system 18 used high OH silica fibers, filter unit 42 utilized an aluminum plate, about 15 cm in diameter and 0.33 cm thick, filters 54 were 10 nm FWHM bandpass, CWL tolerance 2 nm, 50% transmission, blocking complete within 0.01%T, motor 44 was a brushless DC servo, and detector 20 was a silicon photodiode.

One skilled in the art can readily prepare other examples of spectrophotometers from the description of the invention. For example, to practice resonance Raman spectroscopy, a light source 28 would be chosen to have wavelengths that are in resonance with electronic transitions of the analyte of interest. Pass-through filters 54 would be chosen as for standard Raman spectroscopy, but the intensity may be much higher at the detected bands, allowing for better signal at the detector 20. For surface enhanced Raman spectroscopy the sample 14 would be prepared to enhance Raman signals from an analyte. Appropriate sample surfaces are well known to those skilled in the art, and can include electrochemically roughened metal electrodes, metal colloids and sols, metal island films, and the like.

The invention has been described in detail with particular reference to preferred embodiments thereof, but it will be understood that variations and modifications can be effected within the spirit and scope of the invention.

What is claimed is:

1. A postacquired spectrophotometer, for use with a sample and a reference, said spectrophotometer comprising:

a filter unit defining an axis of movement, said filter unit having a plurality of designated sites and a plurality of dark sites disposed in uniform relation to said axis, said designated sites and said dark sites being disposed in alternation, alternating ones of said designated sites having apertures and filters covering said apertures, said filters each transmitting only light of preselected wavelengths, said filter unit having a plurality of actuator pairs each said pair having an integration actuator and a clamping actuator, said actuators being disposed in substantially uniform relation to said axis, said integration actuators each being associated with a respective said designated site, a main member coaxial with said filter unit, said main member having sample and reference beam paths, said beam paths being intersected by said sites, said beam paths each having a cross-section at said filter unit interposable within each said site, said main member having an actuator sensor disposed in operative relation to said actuators, said actuator sensor generating an integration actuator signal upon alignment with each said integration actuator and a clamping actuator signal upon alignment with each said clamping actuator, a drive for continuously moving said filter unit relative to said axis and said beam paths, a detector for producing a signal responsive to light received, a light distribution system directing light separately from said sample and reference to respective said beam paths, and from said beam paths to said detector, and means for processing said signals, said means for processing further comprising a clamping circuit, a plurality of integrators, and a demultiplexer, said clamping circuit in response to each said clamping actuator signal setting a restoration signal proportional to said detector signal, said clamping circuit in response to each said integration actuator signal clamping said detector signal to said restoration signal, said demultiplexer distributing said clamped detector signal to said integrators, said demultiplexer having a single output, said output advancing from one of said integrators to another in repeating sequence in response to one of the members of each said pair of actuator signals.

2. The spectrophotometer of claim 1 further comprising means for repeatedly allocating each integrator to the same filter and beam path.

3. The spectrophotometer of claim 1 wherein said demultiplexer output is advanced in response to said clamping actuator signals.

4. The spectrophotometer of claim 1 wherein each said integration actuator is disposed in substantially uniform spatial relation to a respective said designated site, and each said clamping actuator is disposed in substantially uniform spatial relation to a respective said designated site.

5. The spectrophotometer of claim 1 wherein said filter unit is rotated by said drive about said axis relative to said beam paths.

6. The spectrophotometer of claim 1 wherein said filter unit is reciprocated by said drive along said axis relative to said beam paths.

7. The spectrophotometer of claim 1 wherein said main member has a plurality of said beam path pairs.

8. The spectrophotometer of claim 1 wherein each said integration actuator is a slot in said filter unit.

9. The spectrophotometer of claim 1 further comprising a monochromatic light source, a preconditioning filter, and a pair of conditioning filters, said conditioning filters being complementary to said preconditioning filter, and wherein said light distribution system receives light from said monochromatic light source, directs said light through said preconditioning filter, divides said light into sample and reference beams, directs respective said beams to said sample and reference, directs said beams from said sample and reference through said conditioning filters and along respective said beam paths, and directs said beams, in alternation with each other and with dark periods, from respective said beam paths to said detector.

10. The spectrophotometer of claim 1 wherein said light distribution system further comprises optic fibers.

11. A postacquired spectrophotometer, for use with a sample and a reference, said spectrophotometer comprising:

a filter unit defining an axis of rotation, said filter unit having a plurality of designated sites and a plurality of dark sites disposed in substantially uniform angular relation to said axis, said designated sites and said dark sites being disposed in alternation, alternating ones of said designated sites having apertures, said filter unit having a plurality of actuator pairs each said pair having an integration actuator and a clamping actuator, said actuators being disposed in substantially uniform radial relation to said axis, said integration actuators each being associated with a respective said designated site, filters, each said filter covering a respective said aperture, said filters each transmitting only light of preselected wavelengths, a main member coaxial with said filter unit, said main member having sample and reference beam paths, said beam paths being intersected by said sites, said main member having an actuator sensor disposed in operative relation to said actuators, said actuator sensor generating an integration actuator signal upon alignment with each said integration actuator and a clamping actuator signal upon alignment with each said clamping actuator, a drive continuously rotating said filter unit relative to said axis and said beam paths, a detector for producing a signal responsive to light received, a light distribution system directing light separately from said sample and reference to respective said beam paths, and from said beam paths to said detector, means for processing said signals, said means for processing further comprising a clamping circuit, a plurality of integrators, and a demultiplexer, said clamping circuit in response to each said clamping actuator signal setting a restoration signal proportional to said detector signal, said clamping circuit in response to each said integration actuator signal clamping said detector signal to said restoration signal, said demultiplexer distributing said clamped detector signal to said integrators, said demultiplexer having a single output, said output advancing from one of said integrators to another in repeating sequence in response to one of the members of each said pair of actuator signals, and means for repeatedly allocating each integrator to the same filter and beam path.

12. The spectrophotometer of claim 11 wherein each said apertured designated site defines a geometric sector centered at said axis having a first angular dimension, and each said integration actuator defines a geometric sector centered at said axis, said first and second angular dimensions being substantially equal.

13. The spectrophotometer of claim 12 wherein said demultiplexer output is advanced in response to said clamping actuator signals.

14. The spectrophotometer of claim 13 wherein said main member has a plurality of said beam path pairs.

15. The spectrophotometer of claim 14 further comprising a monochromatic light source, a preconditioning filter, and a pair of conditioning filters, said conditioning filters being complementary to said preconditioning filter, and wherein said light distribution system receives light from said monochromatic light source, directs said light through said preconditioning filter, divides said light into sample and reference beams, directs respective said beams to said sample and reference, directs said beams from said sample and reference through said conditioning filters and along respective said beam paths, and directs said beams, in alternation with each other and with dark periods, from respective said beam paths to said detector.

16. A postacquired spectrophotometer, for use with a sample and a reference, said spectrophotometer comprising:
   a filter unit defining a longitudinal axis, said filter unit being movable along said longitudinal axis, said filter unit having a plurality of designated sites and a plurality of dark sites disposed in uniform spaced relation to said axis, said designated sites and said dark sites being disposed in alternation, alternating ones of said designated sites having apertures and filters covering said apertures, said filter unit having a plurality of actuator pairs each said pair having an integration actuator and a clamping actuator, said actuators having a substantially uniform relation to said axis, said integration actuators each being associated with a respective said designated site,
   a main member coaxial with said filter unit, said main member having sample and reference beam paths, said beam paths being intersected by said sites, said beam paths each having a cross-section at said filter unit interposable within each said site, said main member having an actuator sensor disposed in operative relation to said actuators, said actuator sensor generating an integration actuator signal upon alignment with each said integration actuator and a clamping actuator signal upon alignment with each said clamping actuator,
   a drive for continuously reciprocating said filter unit along said axis relative to said beam paths,
   a detector for producing a signal responsive to light received,
   a light distribution system directing light separately from said sample and reference to respective said beam paths, and from said beam paths to said detector, and
   means for processing said signals, said means for processing further comprising a clamping circuit, a plurality of integrators, and a demultiplexer, said clamping circuit in response to each said clamping actuator signal setting a restoration signal proportional to said detector signal, said clamping circuit in response to each said integration actuator signal clamping said detector signal to said restoration signal, said demultiplexer distributing said clamped detector signal to said integrators, said demultiplexer having a single output, said output advancing from one of said integrators to another in repeating sequence in response to one of the members of each said pair of actuator signals.

17. The spectrophotometer of claim 16 wherein the maximum linear dimension of each said integration actuator and the maximum linear dimension of a respective said designated site are substantially equal.

18. The spectrophotometer of claim 17 wherein said main member has a plurality of said beam path pairs.

19. The spectrophotometer of claim 18 wherein said light distribution system further comprises optic fibers.

20. A multiple sample spectrophotometer, for use with a plurality of samples and at least one reference, said samples each being paired with a reference, said spectrophotometer comprising
   a filter unit movable relative to an axis of movement, said filter unit having a plurality of designated sites and a plurality of dark sites disposed in substantially uniform relation to said axis, said designated sites and said dark sites being disposed in alternation, alternating ones of said designated sites having apertures and filters covering said apertures, said filters each transmitting only light of preselected wavelengths, said filter unit having a plurality of actuator pairs each said pair having an integration actuator and a clamping actuator, said actuators being disposed in substantially uniform relation to said axis, said integration actuators each being associated with a respective said designated site,
   a main member coaxial with said filter unit, said main member having a plurality of pairs of beam paths, said beam paths being intersected by said filter unit sites, said main member having an actuator sensor disposed in operative relation to said actuators, said actuator sensor generating an integration actuator signal upon alignment with each said integration actuator and a clamping actuator signal upon alignment with each said clamping actuator,
   a drive for continuously moving said filter unit relative to said axis and said beam paths,
   at least one detector for producing a signal responsive to light received,
   a light distribution system directing light separately to and from each said sample and reference pair, and to and from associated said beam paths, and to each said detector, and
   means for processing said detector signals, said means for processing further comprising for each said detector: a clamping circuit, a plurality of integrators, and a demultiplexer, said clamping circuit in response to each said clamping actuator signal setting a restoration signal proportional to said detector signal, said clamping circuit in response to each said integration actuator signal clamping said detector signal to said restoration, said demultiplexer distributing said clamped detector signal to said integrators, said demultiplexer having a single output, said output advancing from one of said integrators to another in repeating sequence in response to one of the members of each said pair of actuator signals.

21. The spectrophotometer of claim 20 further comprising a plurality of detectors, each said detector receiving light from a single beam path pair.

22. The spectrophotometer of claim 21 wherein said light distribution system further comprises optic fibers.

23. The spectrophotometer of claim 20 wherein alternating ones of said designated sites have apertures, each said aperture having leading and trailing edges, said edges defining leading and trailing axes perpendicular to said axis of movement, said leading and trailing axes having a separation in a direction of movement of said filter unit defining a designated site dimension, and said actuator pairs each define a pair of actuator axes, said members of each said pair of actuator axes being perpendicular to said axis of movement, said members of each said pair of actuator axes having a separation in a direction of movement of said filter unit defining an actuator dimension, said actuator dimension being substantially equal to said designated site dimension.

24. The spectrophotometer of claim 20 wherein said demultiplexer output is advanced in response to said clamping signals.

25. The spectrophotometer of claim 20 wherein said filter unit is rotated by said drive about said axis relative to said beam paths.

26. The spectrophotometer of claim 20 wherein said filter unit is reciprocated by said drive along said axis relative to said beam paths.

* * * * *